United States Patent
Intoccia

(10) Patent No.: US 7,837,672 B2
(45) Date of Patent: Nov. 23, 2010

(54) ADJUSTABLE DOUBLE BALLOON CATHETER WITH A THROUGH LUMEN FOR STONE MANAGEMENT

(75) Inventor: Al Intoccia, Amherst, NH (US)

(73) Assignee: Boston Scientific Scimed, Inc., Natick, MA (US)

( * ) Notice: Subject to any disclaimer, the term of this patent is extended or adjusted under 35 U.S.C. 154(b) by 456 days.

(21) Appl. No.: 11/638,383

(22) Filed: Dec. 14, 2006

(65) Prior Publication Data

US 2007/0088256 A1    Apr. 19, 2007

Related U.S. Application Data

(62) Division of application No. 10/167,050, filed on Jun. 11, 2002, now abandoned.

(51) Int. Cl.
A61M 1/00 (2006.01)
A61M 29/00 (2006.01)
A61M 37/00 (2006.01)
A61M 31/00 (2006.01)

(52) U.S. Cl. .............. 604/540; 604/101.01; 604/95.03

(58) Field of Classification Search .......... 604/102.02, 604/103.03, 95.03, 96.01, 101.01–101.05, 604/509, 9, 540, 323
See application file for complete search history.

(56) References Cited

U.S. PATENT DOCUMENTS

| | | | |
|---|---|---|---|
| 4,573,966 A | 3/1986 | Weikl et al. | |
| 4,747,826 A | 5/1988 | Sassano | |
| 4,930,496 A * | 6/1990 | Bosley, Jr. | 601/4 |
| 5,135,484 A | 8/1992 | Wright | |
| 5,163,906 A | 11/1992 | Ahmade | |
| 5,275,605 A | 1/1994 | Winkler | |
| 5,281,200 A | 1/1994 | Corso et al. | |
| 5,320,604 A | 6/1994 | Walker et al. | |
| 5,380,284 A | 1/1995 | Don Michael | |
| 5,423,742 A * | 6/1995 | Theron | 604/28 |
| 5,460,610 A * | 10/1995 | Don Michael | 604/101.03 |
| 5,645,529 A | 7/1997 | Fagan et al. | |
| 5,662,609 A | 9/1997 | Slepian | |
| 6,022,336 A | 2/2000 | Zadno-Azizi | |
| 6,120,523 A | 9/2000 | Crocker et al. | |
| 6,156,053 A | 12/2000 | Gandhi et al. | |

(Continued)

FOREIGN PATENT DOCUMENTS

EP    0 474 906    3/1992

OTHER PUBLICATIONS

Delvecchio, et al., "Technique of Endopyelotomy with the Acucise Cutting Balloon," Brazilian Journal of urology, vol. 26(1): pp. 71-75, Jan. - Feb., 2000.

(Continued)

*Primary Examiner*—Nicholas D Lucchesi
*Assistant Examiner*—Rebecca E Eisenberg
(74) *Attorney, Agent, or Firm*—Finnegan, Henderson, Farabow, Garrett & Dunner LLP

(57) ABSTRACT

A method for removing an object from a body lumen includes dispensing fluid into the body lumen, and causing the dispensed fluid to propel the object along the body lumen. A device for removing an object from a body lumen includes a fluid dispenser for dispensing fluid into the body lumen, and a pump in fluid communication with the dispenser.

42 Claims, 5 Drawing Sheets

U.S. PATENT DOCUMENTS

| | | | |
|---|---|---|---|
| 6,251,418 B1 | 6/2001 | Ahern et al. | |
| 6,264,663 B1 | 7/2001 | Cano | |
| 6,287,320 B1 | 9/2001 | Slepian | |
| 6,299,599 B1 | 10/2001 | Pham et al. | |
| 6,461,327 B1 * | 10/2002 | Addis et al. | 604/101.04 |
| 6,485,500 B1 * | 11/2002 | Kokish et al. | 606/194 |
| 2002/0029031 A1 | 3/2002 | Bagaoisan et al. | |

OTHER PUBLICATIONS

Hypro Pumps—"Positive displacement" vs. "Non-positive displacement" [online]. Denver Rubber Company [retrieved on Dec. 5, 2001]. Retrieved from the Internet: <URL: http://www.denverrubber.com/Hypro.htm>.

Bard—Urology Product Tour—Bardex Lubricath Red Latex Double Balloon (40cc and 20cc) Hemostatic Catheter (Coleman Model) [online]. C. R. Bard, Inc., Bard Medical Division [retrieved on Nov. 14, 2001]. Retrieved from the Internet: <URL: http://www.bardmedical.com/urology/cathtour/spec.html>.

Bard Product Catalog—Diagnostic Catheters—Bardex Female Urethrographic Latex Foley Catheter (David Model) [online]. C. R. Bard, Inc., Bard Medical Division [retrieved on Nov. 16, 2001]. Retrieved from the Internet <URL: http://www.bardmedical.com/catalog>.

US 6,056,969, 05/2000, Crittenden (withdrawn)

* cited by examiner

ADJUSTABLE DOUBLE BALLOON CATHETER WITH A THROUGH LUMEN FOR STONE MANAGEMENT

This is a division of application Ser. No. 10/167,050, filed Jun. 11, 2002, now abandoned which is incorporated herein by reference.

TECHNICAL FIELD

The invention relates to minimally invasive medical devices and procedures, and, more particularly, to devices and procedures for removing kidney stones.

BACKGROUND INFORMATION

Various methods exist to remove calculi from body cavities. Calculi, such as those formed in a gall bladder or kidney, can cause significant problems for a patient. For example, ureteral constriction and blockage can cause hydronepherosis, a condition characterized by the damming of urine in the kidneys. A frequent blockage site is the junction of the ureter and the renal pelvis. Acquired blockages are most commonly caused by kidney stones that root themselves in the ureteral lumen wall.

Often, kidney stone removal is performed using stone retrieval devices based on wire baskets, lithotrypsies, pharmaceutical therapeutics or surgery. For example, a cystoscope can be introduced into the ureter to remove an embedded stone. The cytoscope typically includes a wire basket disposed at the distal end. The stone is trapped in the basket, and the cystoscope and trapped stone are then removed from the body.

Existing methods have several deficiencies. These treatments can be difficult to perform, can lead to severe adverse events, and can entail high cost. For example, a retrieval basket can have difficulty trapping calculi of some sizes or shapes. Body tissues can be damaged while spreading the basket and attempting to grasp a stone. A basket may have difficulty grasping a stone that is embedded in a wall of a body lumen. Further, the size of the basket/stone combination may create difficulty in removing the apparatus from the body. Use of ultrasound or solvents can damage body tissues in the vicinity of the stone.

SUMMARY OF THE INVENTION

Methods and devices of the invention enable removal of objects from body lumens with relatively low cost and low incidence of adverse effects. Generally, methods and devices according to invention involve the use of a fluid dispensed into a body lumen to dislodge and/or propel an object in the body lumen. The body lumen can be distended to assist the release of an embedded object.

For example, a kidney stone can be propelled from a ureter into a bladder, without recourse to chemicals, drugs, wire baskets, lithotrypsy or surgery. The invention thus provides an out-patient procedure, that can be performed under a local anesthetic. Some procedures of the invention provide a less painful treatment than many conventional procedures.

Accordingly, in one aspect, the invention features a method for removing an object from a body lumen. The method includes dispensing fluid into the body lumen, and causing the dispensed fluid to propel the object along the body lumen. For example, the object can be a kidney stone lodged in a ureter, and the dispensed fluid propels the stone along the ureter, towards the bladder.

The method can include positioning a fluid dispenser in the body lumen to dispense the fluid. The flow of the dispensed fluid can be impeded in at least one direction through the body lumen. For example, when a kidney stone is being removed from a ureter, the flow of the dispensed fluid can be impeded through the ureter towards the kidney.

In one embodiment, a predetermined quantity of the dispensed fluid is confined within a portion of the body lumen. The portion of the body lumen contains the object. The fluid can be confined by impeding the flow of the fluid at a distal end and at a proximal end of the portion of the body lumen, for example, with clamps or expanded balloons. The predetermined quantity of fluid can be released through the proximal end of the portion of the body lumen to propel the object past the proximal end of the portion of the body lumen.

In some embodiments, the distance between the proximal end and the distal end of the portion of the body lumen is decreased to cause an increase in a fluid turbulence within the body lumen when the fluid is released. Dispensing and releasing predetermined quantities of fluid can be repeated to dislodge and/or propel the object in lumen.

The portion of the body lumen can be allowed to expand while confining the dispensed fluid, to ease the movement of the object through the body lumen.

The fluid can be dispensed at a predetermined pressure level, or dispensed until a predetermined pressure level is attained. The pressure of the dispensed fluid can be varied to dislodge the object from a wall of the body lumen.

The method can further include positioning a distal balloon within the body lumen at a distal end of a portion of the body lumen that contains the object, and positioning a proximal balloon within the body lumen at the proximal end of the portion of the body lumen. The dispensed fluid can then propel the object by pressurizing the proximal balloon to a lower pressure than a pressure of the distal balloon to permit a flow of the fluid past the proximal balloon.

In another embodiment, the pressure of the proximal balloon is decreased after the predetermined quantity of fluid is dispensed. The quantity of fluid can then flow past the proximal end of the portion of the body lumen, to remove the object.

In general, in another aspect, the invention features a device for removing an object from a body lumen. The device includes a fluid dispenser for dispensing a fluid into the body lumen, and a pump in fluid communication with the fluid dispenser, the pump comprising a fluid volume controller configured to provide a sufficient quantity of fluid to cause the object to move through the body lumen. The device includes a distal expansible member, for example, a balloon, in mechanical communication with the fluid dispenser to stabilize the location of the fluid dispenser within the body lumen when the distal expansible member is in an expanded state.

The fluid dispenser defines an aperture through which the fluid is dispensed into the body lumen. Also, a proximal expansible member can be in mechanical communication with the fluid dispenser, with the aperture disposed between the distal and proximal expansible members. Expansion and contraction of the proximal expansible member can then control a flow of the fluid past the proximal expansible member.

The distal expansible member can include a balloon that is inflated to a greater pressure than the pressure of the proximal expansible member, to permit the fluid to flow past the proximal expansible member.

The device can include a pump to pump the fluid to the fluid dispenser. The pump can include a non-positive displacement pump having a preset pressure limit, or a positive displacement pump having a relief valve with a preset pressure limit.

The pump can be built into a handle. The pump can also include a pressure controller configured to provide a sufficient pressure to displace the object in the body lumen.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DESCRIPTION

Figure 1:
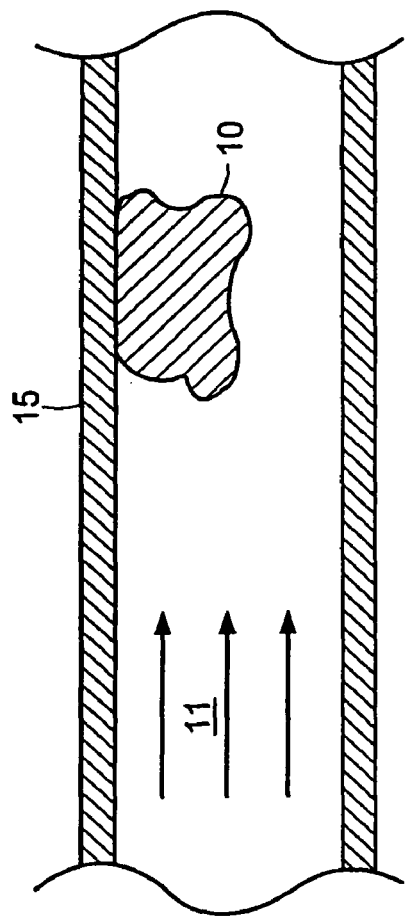
FIG. 1 is a cross-sectional view of a body lumen containing a blockage, which illustrates a method of removing an object from the body lumen, according to general principles of the invention.

Now referring to FIG. 1, general principles of an exemplary embodiment of the invention are described. FIG. 1 is a cross-sectional view of a body lumen containing a blockage. The lumen is defined by a duct 15, for example, a ureter. An object 10, for example, a kidney stone, partially blocks the duct 15. According to a general principle of the invention, a fluid 11 introduced into the duct 15 serves to dislodge the object 10 from the lumen wall of the duct 15 and/or propel the object 10 through the lumen.

If the object 10 is embedded in the wall of the duct 15, it can be dislodged by the flow of the fluid. The fluid can also distend the duct, to help dislodge the object 10, and/or to help move the object 10 through the lumen by increasing the width of the lumen.

Figure 2:
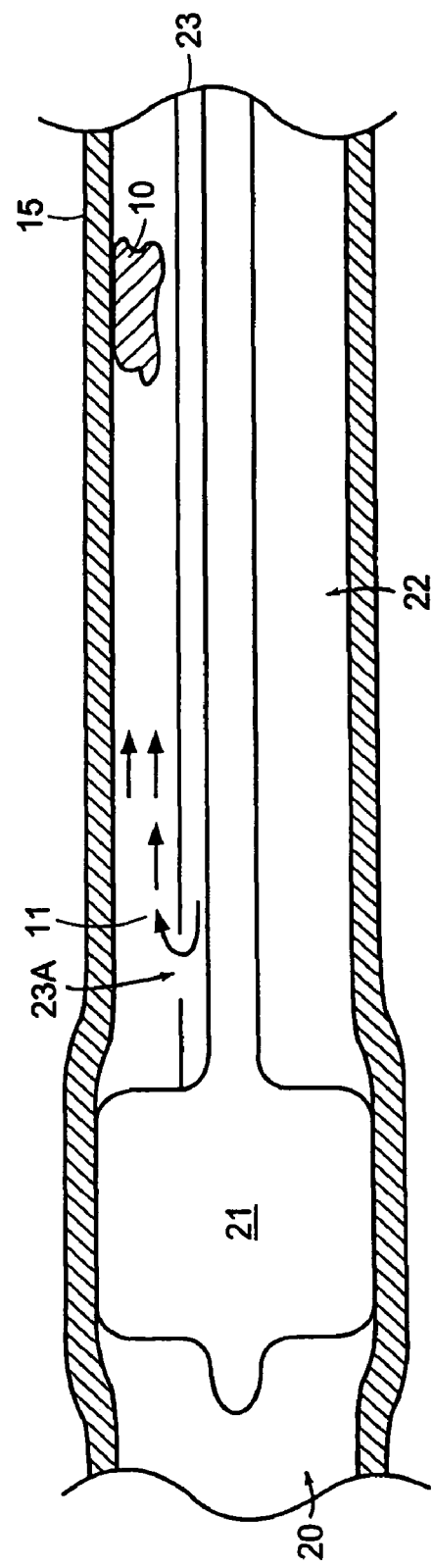
FIG. 2 is a cross-sectional view of an embodiment of a device for removing an object from a body lumen, with the device positioned in a body lumen that has an embedded object.

Now referring to FIG. 2, an embodiment of a device for removing an object from a body lumen is described. FIG. 2 is a cross-sectional view of the device 20 positioned in a body lumen. An object 10 is embedded in the wall of the body lumen. The device 20 includes a catheter 22, a fluid lumen 23 defined by the catheter 22, an aperture 23A that is in fluid communication with the fluid lumen 23, and a member 21 located at a distal end of the catheter 22.

To remove the object 10 from the body lumen, a portion of the catheter 22 is placed within the body lumen, with the member 21 to one side of the object 10. The member 21 then serves to hold the device in position by pressing against the walls of the body lumen. The member 21 may be expansible, and can include, for example, a balloon or a gel. A fluid 11, for example, a saline solution, is directed through the fluid lumen 23. The fluid 11 exits the lumen 23 via the aperture 23A. Movement of the fluid 11 within the body lumen can dislodge the object 10, and can propel the object 10 through the body lumen. The member 21 can block the flow of fluid 11 in a direction that is away from the object 10.

The device 20 can be configured to deliver fluid of a sufficient quantity or pressure to dislodge or propel the object. Further, the quantity of fluid and the pressure of the fluid can be restricted to levels that are unlikely to cause any undesirable side effects for a patient.

Figure 3:
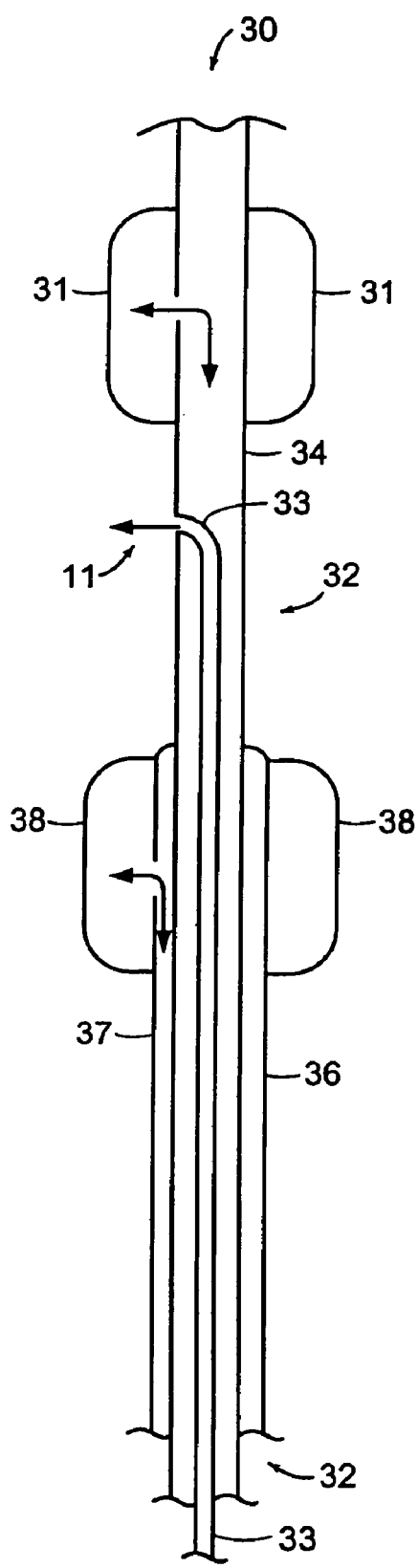
FIG. 3 is a cross-sectional view of an embodiment of a device that includes a fluid dispenser, which includes a catheter.

Now referring to FIG. 3, a preferred embodiment of a device for removing an object from a body lumen is described. FIG. 3 is a cross-sectional view of a device 30. The device 30 includes a fluid dispenser, which includes a first catheter 32, and a second catheter 36. A portion of the first catheter 32 is disposed within the second catheter 36, and can slide with respect to the second catheter 36.

The first catheter includes a fluid lumen 33, through which fluid 11 can be delivered to a body lumen. A distal expansible member 31, is in mechanical communication with the first catheter 32, and a proximal expansible member 38 is in mechanical communication with the second catheter 36.

In a preferred embodiment, the expansible members 31, 38 are balloons. The catheters 32, 36 include lumens 34, 37 for delivery of inflation fluid to the balloons. A fluid, such as a saline solution, can be added or removed from a balloon 31, 38 to control the size of the balloon 31, 38, and to control the pressure of the balloon 31, 38 against the wall of the body lumen.

Now referring to FIGS. 4A-4E, some illustrative embodiments are described of methods for removing an object from a body lumen, which utilize the device 30 of FIG. 3. FIGS. 4A-4E are cross-sectional views of the device 30 in a body lumen, which illustrate steps in some embodiments of methods for removing an object for the body lumen.

Figure 4A:
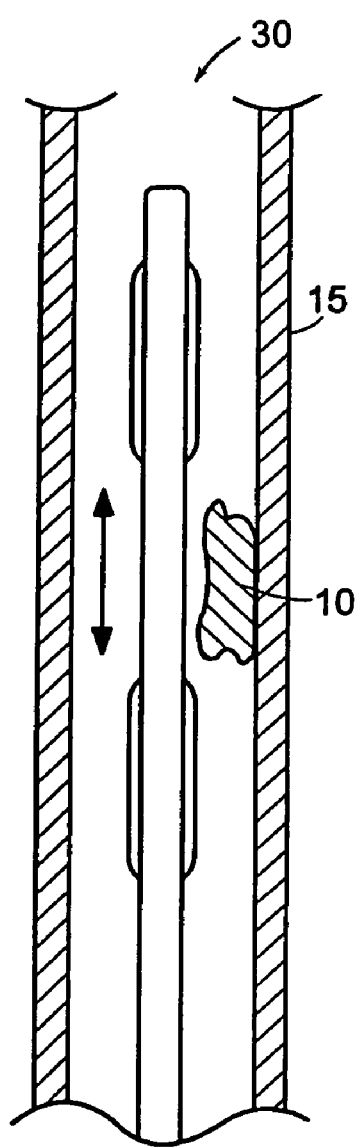
FIGS. 4A-4E are cross-sectional views of the device of FIG. 3 in a body lumen, which illustrate steps in some embodiments of methods for removing an object from the body lumen.
Figure 4B:
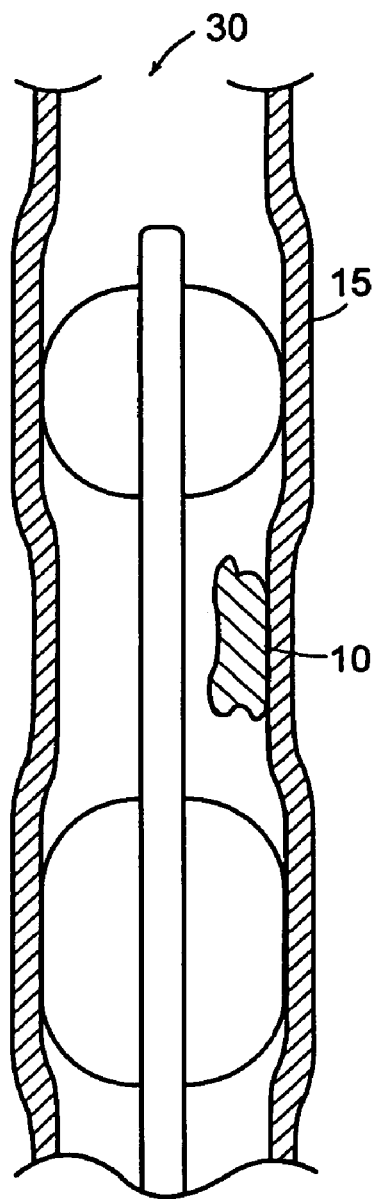
Figure 4E:
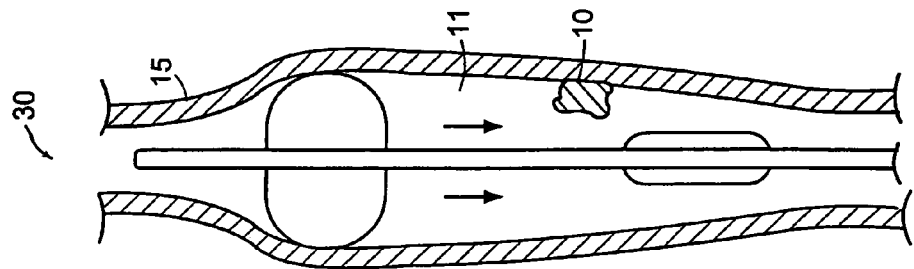

A portion of the device 30 is inserted into the body lumen, while the balloons 31, 38 are in a collapsed state (see FIG. 4A). The spacing between the balloons 31, 38 can be adjusted by sliding the catheters 32, 36 relative to each other (see double arrow in FIG. 4A.) The distal balloon can then be expanded to secure the position of the first catheter 32 within the body lumen (see FIG. 4B).

The proximal balloon 38 can be expanded before, simultaneously with, or after the expansion of the distal balloon 31. In one embodiment, the proximal balloon is inflated to a lower pressure, $P_2$, than the pressure, $P_1$, of the distal balloon. Fluid 11 is then dispensed into the portion of the body lumen defined by the balloons 31, 38. When the pressure of the fluid 11 exceeds that of the pressure of the proximal balloon 38, the fluid 11 begins to flow past the proximal balloon 38. The flow of the fluid 11 against the object 10 can dislodge the object and can propel the object through the lumen, past the proximal balloon 38 (see FIG. 4C.)

In some embodiments, the pressure of the proximal balloon 38 is decreased to enhance the flow of fluid 11, after depositing a predetermined quantity of fluid 11 into the portion of the body lumen, or depositing fluid 11 to a predetermined pressure.

Figure 4D:
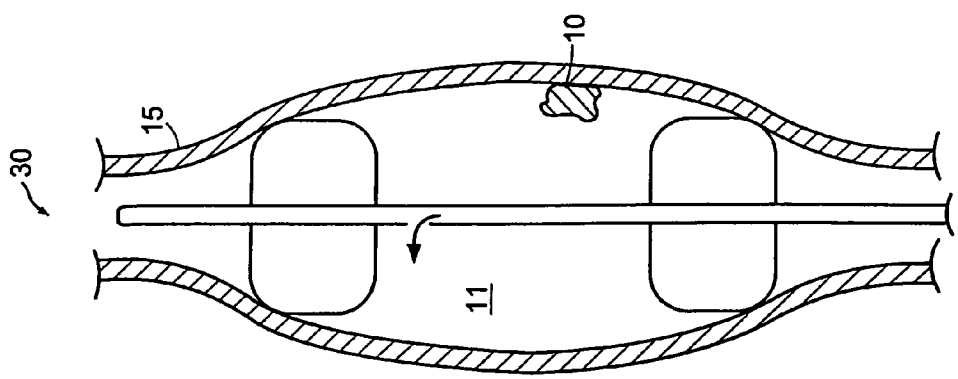
Figure 4C:
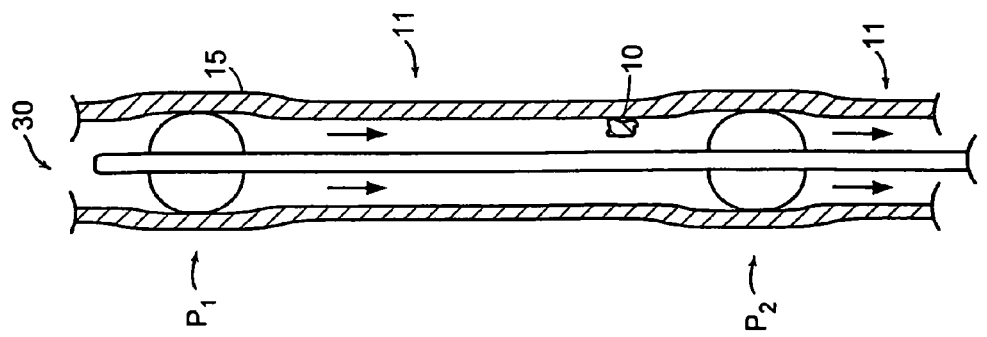

In some embodiments, a predetermined quantity fluid is dispensed while the balloons are fully inflated (see FIG. 4D.) The predetermined quantity of fluid causes the portion of the body lumen to become distended. This stretching of the body lumen can help dislodge the object 10 from the wall of the body lumen. The proximal balloon 38 can then be reduced in size, for example, fully collapsed, to permit the dispensed fluid 11 to flow past the proximal balloon 38 (see FIG. 4E.) The distal balloon 31 remains expanded, in part, to block fluid 11 from flowing in a distal direction past the location of the distal balloon 31.

Dispensing a predetermined quantity of fluid, and releasing the predetermined quantity of fluid, can be repeated until the object is dislodged and/or flushed past the proximal balloon 38. In some embodiments, the fluid 11 is dispensed at a sufficient pressure while the fluid 11 flows against the object 10 to dislodge the object 10 and/or to cause the object to move through the body lumen.

A device can further include aids to help the positioning of the device in the body lumen. For example, a balloon can include radio-opaque markers that provide visibility under fluoroscopic imaging devices.

A device can include balloons that are, for example, selected from those known in the catheter arts. A balloon can include various materials, for example, urethane, silicone or other elastomer. The balloons can have separate inflation supplies, to permit different balloon pressures. The fluid delivered to the body lumen can be a saline solution or other biocompatible materials, for example, other isotonic fluids, for example, a fluorocarbon.

Figure 5:
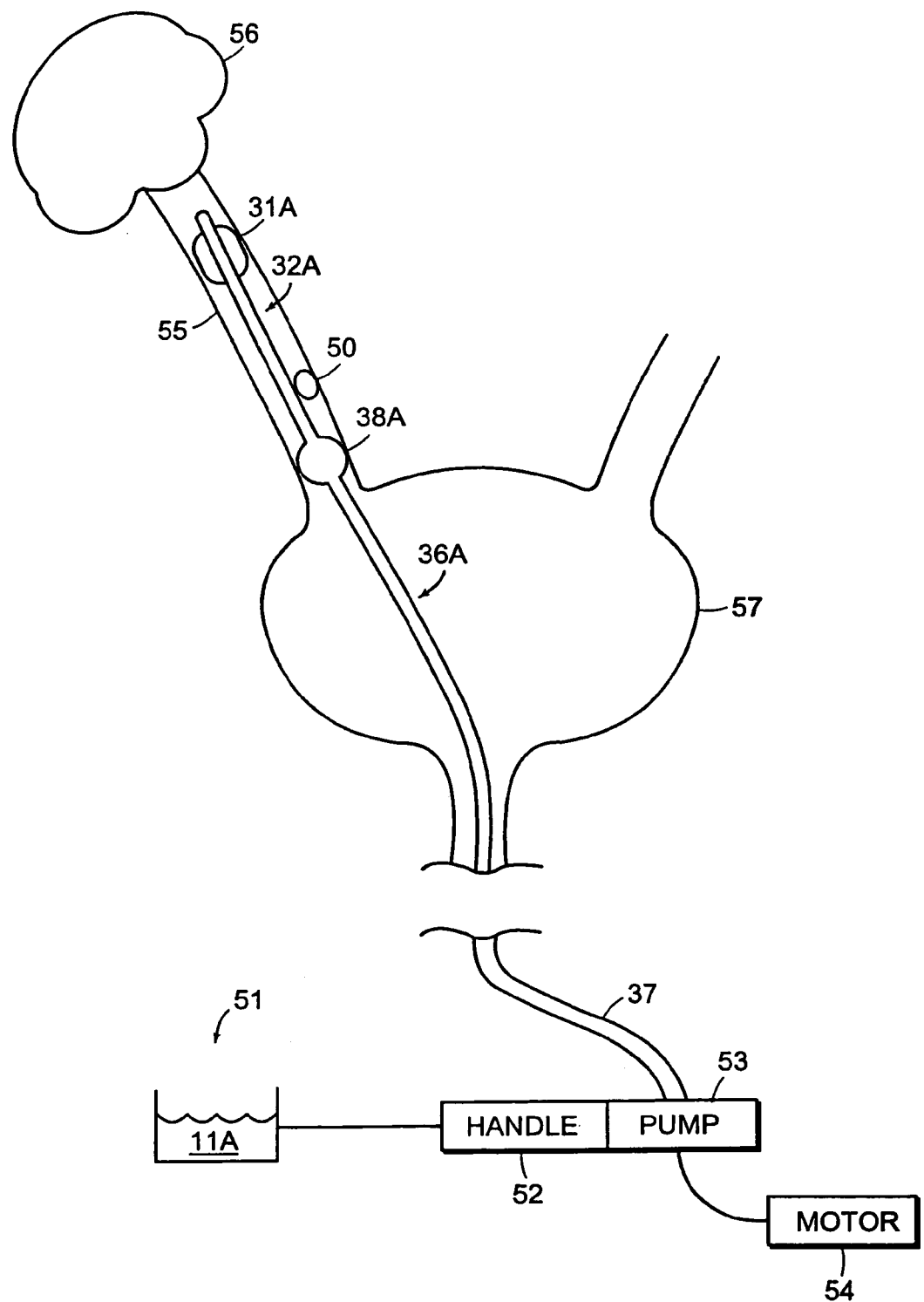
FIG. 5 is a cross-sectional view of an embodiment of a device that is positioned within a ureter for removal of a kidney stone.

Now referring to FIG. 5, embodiments of a device and method of removal of a kidney stone from a ureter are described. FIG. 5 is a cross-sectional view of a device that is positioned within a ureter 55, which leads to a kidney 56, for removal of a kidney stone 50.

The device is similar in construction to the device of FIG. 3. The device includes a catheter 37, which has been inserted through the urethra and bladder 57 into the ureter 55. The ureter 55 is obstructed by the kidney stone 50. A proximal balloon 38A, attached to a second catheter 36A, and a distal balloon 31A, attached to a first catheter 32A, have been positioned on either side of the stone 50.

The catheter 37 extends to a pump 53, which directs saline fluid 11A under pressure to the portion of the ureter 55 that contains the stone 50. The pump 53 is powered by a motor 54, and is held within a handle 52. The device also includes a fluid source 51, which supplies saline fluid 11A to the pump 53. In some embodiments, the pump 53, the motor 54, the handle 52 and/or the fluid source 51 remain outside the body.

In preferred embodiments, the pump 53 includes features that prevent application of a damaging pressure to body tissue. In one embodiment, the pump is a non-positive displacement pump having a preset pressure limit. In another embodiment, the pump is a positive displacement pump having a pressure release, limiting valve.

A preferred embodiment of a method of using the device of FIG. 5 includes advancing the catheter 32A through the urinary tract, under fluoroscopic guidance, to the site of an ingrown stone. The distal balloon 31A is inflated with saline solution once the balloon 31A is at the desired location. The proximal balloon 38A is then advanced with the second catheter 36A, by sliding the second catheter 36A relative to the first catheter 32A, until the distance between the proximal and distal balloons 31A, 38A is at a preferred separation. For example, upon release of a quantity of saline fluid 11A, it is possible to obtain greater fluid velocity and turbulence through use of reduced separation between the balloons 31A, 38A.

A guidewire can be utilized to assist insertion of the device. A variety of suitable guidewires are known to those having experience in the catheter arts.

The proximal balloon 38A is then inflated with saline solution until it exerts a pressure, on the ureter wall, that is less than the pressure exerted by the distal balloon 31A. A tight seal at the distal balloon 31A, and a loose seal at the proximal balloon 38A are obtained. Warm, high-pressure saline is then flushed through the ureter, and the excess flows past the proximal balloon 38A, and into the bladder 57.

The fluid 11A dislodges the stone, and flushes it into the bladder 57. The balloons 31A, 38A are then deflated, and the device is removed from the body. The stone 50 can be removed from the bladder 57 by, for example, conventional means.

A variable spacing between balloons has further advantages. For example, the spacing can be varied to include more than one stone in a body lumen portion, when needed. The spacing can be varied to provide variable saline flush pressures.

Variations, modifications, and other implementations of what is described herein will occur to those of ordinary skill in the art without departing from the spirit and the scope of the invention as claimed. For example: an embodiment of a device can include fixed balloons to provide a more stable configuration and simpler manufacturing; a catheter can include a printed electroactive polymer to provide self-propulsion; balloons can be coated, for example, with hydrogels, drugs or polymers; and a drug can be delivered to the vicinity of an object via the fluid lumen. Accordingly, the invention is to be defined not by the preceding illustrative description but instead by the spirit and scope of the following claims.

What is claimed is:

1. A method for removing an object from a body lumen, comprising:
   dispensing fluid into a portion of the body lumen containing the object;
   impeding a flow of the dispensed fluid at a distal end of the portion of the body lumen and at a proximal end of the portion of the body lumen; and
   causing the dispensed fluid to propel the object along the body lumen,
   wherein during the method for removing the object from the body lumen, a lithotripsy procedure is not performed.

2. The method of claim 1, further comprising positioning a fluid dispenser in the body lumen, and wherein dispensing comprises dispensing the fluid from the fluid dispenser.

3. The method of claim 1, wherein causing the dispensed fluid to propel comprises releasing the flow of the fluid through the proximal end of the portion of the body lumen, to propel the object past the proximal end of the portion of the body lumen.

4. The method of claim 3, further comprising reducing a distance between the proximal end and the distal end of the portion of the body lumen to cause an increase in a fluid turbulence within the body lumen when the fluid is released.

5. The method of claim 3, wherein dispensing and causing the dispensed fluid to propel are repeated to dislodge the object from a wall of the body lumen.

6. The method of claim 1, wherein impeding comprises causing the portion of the body lumen to expand to ease a movement of the object.

7. The method of claim 1, wherein causing the dispensed fluid to propel comprises dispensing fluid until a predetermined pressure level of the fluid is reached.

8. The method of claim 1, wherein dispensing comprises causing a pressure of the dispensed fluid to vary to dislodge the object from a wall of the body lumen.

9. The method of claim 1, further comprising: positioning a distal balloon within the body lumen at the distal end of the portion of the body lumen that contains the object; and positioning a proximal balloon within the body lumen at the proximal end of the portion of the body lumen, and wherein causing the dispensed fluid to propel comprises pressurizing the proximal balloon to a lower pressure than a pressure of the distal balloon to permit a flow of the fluid past the proximal balloon.

10. The method of claim 1, wherein the body lumen comprises a ureter, and wherein causing the dispensed fluid to propel includes causing the dispensed fluid to propel a kidney stone along the ureter into a bladder.

11. A method for removing an object from a body lumen, comprising:
   inserting a medical device into the body lumen, the medical device having a fluid dispenser;
   dispensing fluid into the body lumen;
   causing the dispensed fluid to propel the object along the body lumen, and
   impeding a flow of the dispensed fluid in at least one direction through the body lumen,
   wherein during the method for removing the object from the body lumen, a lithotripsy procedure is not performed.

12. The method of claim 11, further comprising confining a predetermined quantity of dispensed fluid within a portion of the body lumen that contains the object by positioning a portion of the medical device within the body lumen such that a distal expansible member is located distal of the object and a proximal expansible member is located proximal of the object; and wherein causing the dispensed fluid to propel includes releasing the fluid from the portion of the body lumen.

13. The method of claim 11, wherein the at least one direction is through a ureter towards a kidney.

14. A method of displacing an object within a body lumen, comprising:
   inserting into the body lumen a medical device comprising:
      a fluid dispenser defining an aperture for dispensing a fluid into the body lumen;
      a distal expansible member connected to the fluid dispenser and located distal of the aperture; and
      a proximal expansible member located proximal of the aperture, both the distal and proximal expansible members configured for deployment between a collapsed state and an expanded state;
   positioning a portion of the medical device within the body lumen such that the distal expansible member is located distal of the object;
   expanding the distal expansible member until it seals against a wall of the body lumen;
   dispensing fluid through the aperture and into the body lumen; and
   wherein the dispensed fluid causes displacement of the object such that the object and a portion of the fluid flows proximally past the proximal expansible member and in between the wall of the body lumen and an outer surface of the proximal expansible member, wherein during the method for displacing the object within the body lumen, a lithotripsy procedure is not performed.

15. The method of claim 14, further comprising, prior to dispensing fluid:
   positioning the proximal expansible member proximal of the object; and
   expanding the proximal expansible member until it seals against a wall of the body lumen.

16. The method of claim 15, wherein the proximal expansible member is expanded before the distal expansible member is expanded.

17. The method of claim 15, wherein the proximal expansible member is expanded approximately simultaneous with the expansion of the distal expansible member.

18. The method of claim 15, wherein the proximal expansible member is expanded after the distal expansible member is expanded.

19. The method of claim 15, further comprising, after dispensing the fluid, partially collapsing the proximal expansible member.

20. The method of claim 15, wherein the proximal expansible member is expanded to a lower pressure than that of the distal expansible member.

21. The method of claim 20, wherein the fluid is dispensed such that a pressure of the fluid exceeds a pressure of the proximal expansible member.

22. The method of claim 15, wherein the proximal and distal expansible members are slidable relative to each other, and wherein positioning the proximal expansible member comprises sliding the proximal expansible member relative to the distal expansible member.

23. The method of claim 14, further comprising repeatedly dispensing fluid into the body lumen in order to further displace the object.

24. The method of claim 14, wherein the distal and proximal expansible members comprise balloons, each balloon being individually inflated and configured for inflation to different pressures.

25. The method of claim 14, wherein the object comprises a kidney stone.

26. The method of claim 14, wherein the body lumen comprises a ureter.

27. A method of displacing an object within a body lumen, comprising:
   inserting into the body lumen a medical device comprising:
      a fluid dispenser defining an aperture for dispensing a fluid into the body lumen;
      a distal expansible member connected to the fluid dispenser and located distal of the aperture; and
      a proximal expansible member located proximal of the aperture, both the distal and proximal expansible members configured for deployment between a collapsed state and an expanded state;
   positioning a portion of the medical device within the body lumen such that the distal expansible member is located distal of the object;
   expanding the distal expansible member until it seals against a wall of the body lumen;
   positioning the proximal expansible member proximal of the object;
   expanding the proximal expansible member until it seals against a wall of the body lumen;
   after positioning the proximal expansible member proximal of the object and expanding the proximal expansible member until it seals against a wall of the body lumen, dispensing fluid through the aperture and into the body lumen;
   releasing the dispensed fluid to cause displacement of the object such that object and a portion of the fluid flows proximally past the proximal expansible member and in between the wall of the body lumen and an outer surface of the proximal expansible member,
   wherein the distal and proximal expansible members are expanded to substantially the same extent and wherein the dispensed fluid distends the body lumen in order to stretch the body lumen and dislodge an embedded object from the body lumen, and
   wherein during the method for displacing the object within the body lumen, a lithotripsy procedure is not performed.

28. A method of displacing an object within a body lumen, comprising:
   inserting into the body lumen a medical device comprising:
      a fluid dispenser defining an aperture for dispensing a fluid into the body lumen;
      a distal expansible member connected to the fluid dispenser and located distal of the aperture; and
      a proximal expansible member located proximal of the aperture, both the distal and proximal expansible members configured for deployment between a collapsed state and an expanded state;
   positioning a portion of the medical device within the body lumen such that the distal expansible member is located distal of the object;
   expanding the distal expansible member until it seals against a wall of the body lumen;
   positioning the proximal expansible member proximal of the object;
   expanding the proximal expansible member until it seals against a wall of the body lumen;
   after positioning the proximal expansible member proximal of the object and expanding the proximal expansible member until it seals against a wall of the body lumen, dispensing fluid through the aperture and into the body lumen;
   partially collapsing the proximal expansible member, after dispensing the fluid;
   wherein the dispensed fluid causes displacement of the object such that the object and a portion of the fluid flows proximally past the proximal expansible member and in between the wall of the body lumen and an outer surface of the proximal expansible member,
   wherein during the method for displacing the object within the body lumen, a lithotripsy procedure is not performed, and
   wherein the body lumen comprises a ureter, and the fluid displaces the object closer to the bladder.

29. A method of displacing an object within a body lumen, comprising:
   inserting into the body lumen a medical device comprising:
      a fluid dispenser defining an aperture for dispensing a fluid into the body lumen;
      a distal expansible member connected to the fluid dispenser and located distal of the aperture; and
      a proximal expansible member located proximal of the aperture, both the distal and proximal expansible members configured for deployment between a collapsed state and an expanded state;
   positioning a portion of the medical device within the body lumen such that the distal expansible member is located distal of the object;
   expanding the distal expansible member until it seals against a wall of the body lumen;
   positioning the proximal expansible member proximal of the object;
   expanding the proximal expansible member until it seals against a wall of the body lumen;
   after positioning the proximal expansible member proximal of the object and expanding the proximal expansible member until it seals against a wall of the body lumen, dispensing fluid through the aperture and into the body lumen;
   wherein the proximal expansible member is expanded to a lower pressure than that of the distal expansible member,
   wherein the fluid is dispensed such that a pressure of the fluid exceeds a pressure of the proximal expansible member,
   wherein the dispensed fluid causes displacement of the object such that the object and a portion of the fluid flows proximally past the proximal expansible member and in between the wall of the body lumen and an outer surface of the proximal expansible member,
   wherein during the method of displacing the object within the body lumen, a lithotripsy procedure is not performed; and
   wherein the body lumen comprises a ureter, and the fluid displaces the object closer to the bladder.

30. A method of displacing an object within a ureter, comprising:
   inserting into the ureter a medical device comprising:
      a fluid dispenser defining an aperture for dispensing a fluid into the ureter;
      a distal expansible member connected to the fluid dispenser and located distal of the aperture; and
      a proximal expansible member located proximal of the aperture, both the distal and proximal expansible members configured for deployment between a collapsed state and an expanded state;
   positioning a portion of the medical device within the ureter such that the distal expansible member is located distal of the object;
   expanding the distal expansible member until it seals against a wall of the ureter;
   dispensing fluid through the aperture and into the ureter; and
   wherein the dispensed fluid causes displacement of the object such that the object and a portion of the fluid flows proximally past the proximal expansible member, and
   wherein during the method of displacing the object within the ureter, a lithotripsy procedure is not performed.

31. The method of claim 30, further comprising, prior to dispensing fluid: positioning the proximal expansible member proximal of the object; and
   expanding the proximal expansible member until it seals against a wall of the ureter.

32. The method of claim 31, wherein the proximal expansible member is expanded before the distal expansible member is expanded.

33. The method of claim 31, wherein the proximal expansible member is expanded approximately simultaneous with the expansion of the distal expansible member.

34. The method of claim 31, wherein the proximal expansible member is expanded after the distal expansible member is expanded.

35. The method of claim 31, wherein the distal and proximal expansible members are expanded to substantially the same extent and wherein the dispensed fluid distends the ureter in order to stretch the ureter and dislodge an embedded object from the ureter.

36. The method of claim 31, further comprising, after dispensing the fluid, partially collapsing the proximal expansible member.

37. The method of claim 31, wherein the proximal expansible member is expanded to a lower pressure than that of the distal expansible member.

38. The method of claim 37, wherein the fluid is dispensed such that a pressure of the fluid exceeds a pressure of the proximal expansible member.

39. The method of claim 31, wherein the proximal and distal expansible members are slidable relative to each other, and wherein locating the proximal expansible member comprises sliding the proximal expansible member relative to the distal expansible member.

40. The method of claim 30, further comprising repeatedly dispensing fluid into the ureter in order further displace the object.

41. The method of claim 30, wherein the distal and proximal expansible members comprise balloons, each balloon being individually inflated and configured for inflation to different pressures.

42. The method of claim 30, wherein the dispensed fluid flows proximally past the proximal expansible member and in between the wall of the ureter and an outer surface of the proximal expansible member.

* * * * *

UNITED STATES PATENT AND TRADEMARK OFFICE
CERTIFICATE OF CORRECTION

Page 1 of 1

PATENT NO. : 7,837,672 B2
APPLICATION NO. : 11/638383
DATED : November 23, 2010
INVENTOR(S) : Al Intoccia It is certified that error appears in the above-identified patent and that said Letters Patent is hereby corrected as shown below:

In claim 40, column 11, line 2, after "in order", insert --to--.

Signed and Sealed this
Eighth Day of March, 2011

David J. Kappos
*Director of the United States Patent and Trademark Office*